United States Patent [19]

Dowden et al.

[11] 4,005,048

[45] Jan. 25, 1977

[54] TREATING HYDROCARBONS

[75] Inventors: Dennis Albert Dowden; Ian Robertson Shannon; Michael Staines Spencer, all of Stockton-on-Tees, England

[73] Assignee: Imperial Chemical Industries Limited, London, England

[22] Filed: May 7, 1974

[21] Appl. No.: 467,800

Related U.S. Application Data

[62] Division of Ser. No. 245,882, April 21, 1972, Pat. No. 3,857,901.

[30] Foreign Application Priority Data

Apr. 27, 1971 United Kingdom ............ 11548/71

[52] U.S. Cl. .............................. 252/432; 252/437; 252/440; 252/441; 252/442; 252/454; 252/455 R; 252/457; 252/461; 252/462; 252/463; 252/471; 260/668 A; 260/672 R; 260/672 T

[51] Int. Cl.$^2$ ...................... C07C 3/58; C07C 5/24

[58] Field of Search ...................... 260/668 A, 672; 252/461, 462, 463, 467, 471, 432, 475, 440, 437, 442, 455 R, 441, 454, 457

[56] References Cited

UNITED STATES PATENTS

| | | | |
|---|---|---|---|
| 3,328,478 | 6/1967 | Barclay et al. | 252/461 X |
| 3,334,962 | 8/1967 | Clearfield | 252/461 X |
| 3,450,789 | 6/1969 | Kehl | 252/462 X |
| 3,649,560 | 3/1972 | Croce et al. | 252/432 |
| 3,660,480 | 5/1972 | Pregaglia et al. | 252/467 X |

*Primary Examiner*—Patrick P. Garvin
*Attorney, Agent, or Firm*—Cushman, Darby & Cushman

[57] ABSTRACT

Hydrocarbon catalytic reactions (including isomerization, cyclization, aromatization, disproportionation, alkylation, de-alkylation, reforming, hydrcracking) are effected over a catalyst comprising a crystalline solid solution of two or more irreducible compounds differing in the valency of their cations and/or their anions. The catalysts may be made by heating together the components of the crystalline solid solution or compounds thermally decomposable thereto. Some of the catalysts contain one or more additional acidic materials which act as co-catalysts, and are new compositions of matter.

6 Claims, No Drawings

TREATING HYDROCARBONS

This is a division of application Ser. No. 245,882, filed Apr. 21, 1972, now U.S. Pat. No. 3,857,901.

This invention relates to a catalytic process of treating hydrocarbons for the purpose particularly of causing cracking, isomerisation, disproportionation and related reactions, and also polymerisation and addition or removal of molecular fragments, that is, principally, reactions which are said to be acid-catalysed.

According to the invention a process of treating hydrocarbons comprises contacting them with a catalyst comprising a crystalline solid solution of two or more irreducible compounds differing in the valency of their cations or their anions or both.

Such crystalline solid solutions have crystal lattice defects and it is believed their catalytic activity is due in part to such defects.

In an ideal crystal, each ion is situated on the appropriate lattice site and each lattice site is occupied by the appropriate ion. Such a crystal has an accurately stoichiometric formula but can only be in thermodynamic equilibrium at the absolute zero of temperature since it then has effectively zero configurational entropy, whereas at higher temperatures all crystals must deviate to some extent from the perfect state owing to the occurrence of lattice defects.

From general studies of lattice defects seven types of primary imperfections are recognised (see, for example, Shockley, W., Holloman, J. H., Maurer, R. and Seitz, F., "Imperfections in Nearly Perfect Crystals," Wiley, New York, 1952, pp. 3–76):

1. Phonons
2. Electrons and positive holes
3. Excitons
4. Vacant lattice sites and interstitial atoms or ions.
5. Impurity atoms in either interstitial or substitutional positions.
6. Dislocations
7. Stacking faults Types 4 and 5 may be called "equilibrium atomic defects" (Greenwood, N. N., "Ionic Crystals, Lattice Defects and Nonstoichiometry", Butterworth, London, 1968, pp. 62–63) and are most closely related to the chemical properties of crystals. Such defects fall into two categories:

a. those which are inherent in the thermodynamics of the solid state and which must occur in all crystals, but usually in only small concentrations unless the temperature is close to the melting point of the crystal;
b. those which are specific to the particular crystalline compound considered.

The defects on which the process of the invention depends fall into category (b). A solid can possess cation and/or anion specific defects (vacancies or interstitials), but only in crystalline solids do the defects occupy definite and reproducible positions.

These defects may occur at random or in an ordered way.

Cation (or anion) vacancies can be brought about by:

1. Insertion of cations (or anions) of higher charge into the sub-lattice of cations (or anions, respectively);
2. Insertion of cations (or anions) into interstitial positions;
3. Insertion of anions (or cations) of lower charge into the sub-lattice.
4. Removal of interstitial anions (or cations).

Sometimes vacancies can be produced by more than one of these mechanisms.

It will be appreciated that the crystalline solid solutions on which the process of the invention depends are different from mixed oxide materials previously proposed as catalysts for hydrocarbon treatment processes. Many of such mixed oxide materials are amorphous, according to X-ray deffraction, and typical of those that are crystalline are the aluminosilicates, which are chemical compounds in their own right arranged in a crystal lattice, such as a zeolite lattice, which is characteristic of the compound. Similarly, spinels are not solid solutions.

In the crystalline solid solutions according to our invention, the lattice of one of the components (which may be a compound) is maintained but is made defective as described above.

In this specification the term "irreducible" is used in the normal chemical sense, to denote that no extensive reduction to a lower valency state or to the element occurs under process conditions in which hydrocarbons are treated, that is, at temperatures up to 1000° C and pressures up to 100 atmospheres, for example. However, small amounts of reduction (particularly of surface ions) which can give rise to semi-conductivity and which may promote redox or other side reactions, are not excluded.

Preferably the crystalline solid solutions are of compounds of two or more lattice cation-forming elements of differing valency between 2 and 6 inclusive. The elements of highest valency (ie. 5 and 6) include phosphorus, arsenic, vanadium, niobium, tantalum, antimony, chromium, molybdenum and tungsten. Suitable tetravalent elements include silicon, germanium, tin, titanium, zirconium, hafnium, cerium, thorium and uranium. Suitable lower-valency elements include magnesium, calcium, strontium, barium, boron, scandium, chromium, manganese, iron, cobalt, nickel, copper, zinc, yttrium, lanthanum, the rare earth elements and aluminium.

Especially preferred are the crystalline solid solutions in which the valencies of the cation-forming elements are 4 and 2, or 4 and 3, or 3 and 2.

The components of the crystalline solid solutions are preferably oxides. One particular preference is that the higher-valency element is in excess (by atoms), so that the crystal lattice of the oxide of the element of higher valency is made defective by the presence of the oxide of the element of lower valency. This is observed to result in crystal lattice changes consistent with the formation of anion defects (oxygen vacancies), over-all electrical neutrality being preserved.

When the higher-valency element is in excess (by atoms) it will be appreciated that the cations of the trivalent elements may be in excess or in deficiency according as the other cations are those of a divalent or tetravalent element. More than one lower-valent or higher-valent oxide may be present. In addition small quantities of oxides of elements of higher valency than those of the main lattice (for example of pentavalent niobium or tantalum in a zirconia lattice) may be in solution, provided that anion vacancies are still present and that the main lattice structure is maintained.

The proportion of the lower valent element depends on its solubility in the higher-valent compound, but is usually at least 0.05%, especially 1-30% and more preferably 5-25%. These percentages are by metal atoms. The concentration of defects in the lattice is preferably greater than 1%.

The compound forming the main lattice is preferably of the type $AX_2$, in which A is cation-forming and X is anion-forming. The main lattice has preferably a monoclinic or tetragonal or more especially a cubic (fluorite) structure. Very suitable main lattice compounds are zirconia and hafnia.

In preferred catalysts for use in the process of the invention there is contained one or more additional acidic materials which act as "co-catalysts". This may for example be introduced with the anion of a strong acid. Such anions, for example sulphate, chloride, fluoride and phosphate, appear to be bound strongly to the crystalline material in a water-insoluble form; and they are found to increase its catalytic activity substantially for many reactions. Other substances not normally considered as strong acids, but which interact with the crystalline solid solution to form acidic centres, may be used alternatively or with the strong acid anion; examples are silica and boria.

The proportion of additional acidic material is preferably more than 0.1% by weight, especially 0.5 to 20%.

The invention provides also methods of making the catalysts, which comprises heating together the components of the crystalline solid solution or compounds thermally decomposable thereto. The formation of the crystalline solid solution occurs at a lower temperature the smaller the particle size of the components or compounds decomposable thereto. In one such method a mixture of thermally decomposable compounds of constituent metals, together with an organic chelating compound and a solvent, is evaporated to dryness and calcined to give metal oxides at a sufficiently high temperature to produce a crystalline solid solution of the oxides. Suitable chelating compounds are citric acid and other hydroxy-acids for example glycollic, lactic, malic or tartaric acids.

In another such method the solid solution of oxides is formed by co-precipitation of hydrous oxides, hydroxides, carbonates or oxalates, followed by calcination. Suitable precipitants include ammonia, sodium hydroxide and ammonium or sodium carbonate.

Other methods of bringing the metal oxides or compounds thermally decomposable to oxides into sufficiently intimate association, for example, milling under shear and hydrolysis of alkoxides may be used.

Particularly when co-precipitation by an alkali metal compound has been employed the crystalline solid solution may with advantage be treated with aqueous acid or an ammonium salt solution. This treatment is suitably effected after the calcination.

Preferably in making the crystalline solid solution a compound is used which will introduce the anion of a strong acid, such as the ammonium salt or (less preferably) the acid itself. This may be effected as a distinct step or it may suffice to rely on such an anion being introduced as impurity in a starting material, for example sulphate in zirconium nitrate. The stage at which the radical is introduced depends on which radical is used. Thus for example sulphate may be introduced at any stage, most conveniently before the solid solution has been formed, but phosphate is preferably introduced after the solid solution has been formed.

The temperature of the calcination varies according to which substances are to be present in the crystalline solid solution and to their state of subdivision, as mentioned. In normal practice the temperature is chosen by reference to an X-ray diffraction examination of the calcined material. Typical temperatures are above 550° C for a wide range of substances when calcination is in normal atmospheric air and for a convenient time, say 1-24 hours. Temperatures above 1100° C are not usually necessary. In order to avoid decreasing the active surface of the catalyst unduly, the calcination should be as short and at as low a temperature as will produce the solid solution. In addition any other methods of producing catalysts of high surface area or of preventing sintering or aggregation of particles during drying or calcination may be employed. These methods include freeze-drying, use of non-aqueous solvents and incorporation of an inert material to separate the catalyst particles during calcination.

The crystalline solid solutions containing additional acid are believed to be new compositions of matter.

The catalysts as prepared above may be used directly as hydrocarbon conversion catalysts. They may also be used after incorporation of metals or metal compounds (by impregnation or other means), having oxidizing and/or reducing properties and especially those having hydrogenating - dehydrogenating properties.

If desired, the catalysts may be incorporated in any suitable way with a matrix, generally comprising one or more porous inorganic oxides, which can serve as a binder and, if suitably chosen, may serve as an auxiliary catalyst. Such matrices include silica, alumina, silica-alumina and other oxide mixtures containing alumina or silica.

The catalysts may also be used when supported on a carrier having a relatively high surface area, that is, over about 100 m²/g. Suitable carriers include substantially any porous solid material of suitable heat or steam stability, such as the inorganic oxides mentioned above.

The term "treating hydrocarbons" is to be understood as including a variety of hydrocarbon catalytic reactions ranging from isomerisation reactions in which the carbon chain is modified slightly, for example in the direction of more branching, through more drastic modifications such as cyclisation and aromatisation, disproportionation, cracking and dealkylation, to cracking into substantially gaseous products. These reactions may be carried out in the presence of hydrogen, steam or carbon oxides or mixtures of these as reactants or diluents. Furthermore the term "hydrocarbon" is to be understood as extending to derivatives of hydrocarbons, containing for example oxygen, nitrogen or sulphur, such as are commonly treated in the chemical and petroleum industries, in their own right or as impurities in hydrocarbons. More specifically the reactions include catalytic cracking of gas oils; catalytic reforming of naphthas and hydrocracking of gas oils and heavier feeds to produce gasoline and petrochemical feedstocks; and alkylation of olefines with isoparaffins to produce highly branched paraffins in the gasoline boiling range, for example the reaction of isobutane with butene.

A particular example of a process according to the invention is the isomerisation of ortho-xylene to meta- and para-xylene, which may be suitably carried out at temperatures in the range 400° to 500° C and pressures suitably about 1 atmosphere absolute. The throughput of ortho-xylene can be for example 0.1 to 1.0 grams per gram of catalyst per hour.

Another is the cracking of hydrocarbons into smaller molecules, for example the splitting-off of alkyl groups from relatively stable alkyl-substituted aromatic hydrocarbons to produce unsubstituted aromatic hydrocarbons. This may be carried out at temperatures in the range 500° to 800° C and pressures in the range up to 60 at., for example 30 to 50 at., in the presence of hydrogen. More reactive hydrocarbons, for example cumene, are dealkylated under milder conditions, for example 300°–500° C.

In some of the hydrocarbon treatment processes carried out according to the invention the catalyst tends to lose activity, apparently owing to carbon laydown, but this activity can be substantially restored by heating in a current of air, conveniently in the reactor in which the hydrocarbon treatment is carried out.

In the following Examples, which do not restrict the scope of our invention, the activity of a range of catalysts is assessed by reference to the reactions in which cumene is cracked to benzene and propylene or in which ortho-xylene is isomerised. In the experimental runs the hydrocarbon vapour was passed through a bed of catalyst at 1 at. pressure without a carrier gas. Test runs lasted up to 6 hours and liquid samples of product were analysed during runs. For the cumene experiments the catalyst was calcined at 580° C after each run and re-used.

EXAMPLE 1

Zirconia/magnesium oxide solid solution prepared by the co-precipitation method from zirconyl nitrate containing sulphate. 110.9 g zirconyl nitrate (40% $ZrO_2$) and 12.8 g magnesium nitrate were dissolved in 300 ml distilled water. An ammonia solution was made up containing 91 ml 32% $NH_4OH$ and diluted to one litre. The mixed nitrates were added rapidly to the ammonia solution with vigorous stirring. The product was filtered and washed four times with distilled water, dried under vacuum at 120° C and then calcined at 600° C. Its percentage composition by weight was $ZrO_2$ 91.1; MgO 3.6; S 0.6; and its surface area was 63 $m^2g^{-1}$. An X-ray diffraction examination showed it to be cubic zirconia of lattice parameter 5.085A (indicating approximately 10 mole % MgO in solid solution) and crystallite size about 130A. No free MgO was detected.

The catalyst was mixed with 1% graphite and compressed into ⅛ inch pellets. When tested for activity in cumene cracking at 450° C, atmospheric pressure and weight hourly spaced velocity (WHSV) of 3.9 g $g^{-1}hr^{-1}$, the results were:

TABLE 1

| Time (min) | Cumene Conversion (mole %) |
|---|---|
| 6 | 65.4 |
| 20 | 37.0 |
| 40 | 23.5 |
| 60 | 15.3 |

When tested for activity in ortho-xylene isomerisation at 400° C, atmospheric pressure and weight hourly space velocity of 0.31 the results were:

TABLE 2

| Time | Conversion | Pass yield, mole % | |
|---|---|---|---|
| hours | mole % | para- + meta-xylene | toluene |
| 0.5 | 38.5 | 31.5 | 3.5 |
| 1.0 | 38.0 | 31.2 | 3.4 |
| 1.5 | 20.6 | 15.0 | 2.8 |
| 2.0 | 11.4 | 7.0 | 2.2 |
| 3.0 | 7.8 | 3.4 | 2.2 |

The product at 1 hour was analysed and found to contain 49 mole % of para-xylene and 26.3 mole % of meta-xylene.

EXAMPLE 2

Low-sulphate zirconia/magnesium oxide solid solution prepared by the co-precipitation method from zirconyl carbonate.

For this catalyst preparation, which was otherwise as in Example 1, 77.1 g zirconyl carbonate were dissolved in nitric acid, the solution diluted to 400 mls and 18.5 g magnesium nitrate added. The catalyst had the percentage composition by weight: $ZrO_2$, 86.2; MgO, 7.6; S, 0.08; and its surface area was 70 $m^2 g^{-1}$.

An X-ray diffraction examination showed it to be cubic zirconia of lattice parameter about 5.06A (indicating a large amount of MgO in solid solution) and crystallite size about 120A. No free MgO was detected.

When tested for cumene cracking at 450° C and WHSV 4.2 g $g^{-1}hr^{-1}$, benzene was found in the product, but in considerably smaller quantities.

EXAMPLE 3

Zirconia/alumina solid solution prepared by the co-precipitation method from zirconyl nitrate containing sulphate.

The catalyst was prepared from 111 g zirconyl nitrate and 37.5 g aluminium nitrate in a similar manner to Example 1 except that the calcination was at 750° C in order to obtain the crystalline solid solution. Its percentage composition by weight was $ZrO_2$, 86.2; $Al_2O_3$, 7.6; S 1.0: and its surface area was 109 $m^2g^{-1}$. An X-ray diffraction examination showed it to be a cubic zirconia of lattice parameter 5.08A (indicating $Al_2O_3$ in solid solution) and crystallite size about 75A. No free $Al_2O_3$ was detected.

When this catalyst was tested for activity in cumene cracking the results were:

TABLE 3

| Reactor Temperature (° C) | WHSV (gg$^{-1}$hr$^{-1}$) | Time (min) | Cumene Conversion (mole %) |
|---|---|---|---|
| 400 | 4.1 | 6 | 66.5 |
| | | 20 | 43.8 |
| | | 40 | 36.6 |
| | | 60 | 34.1 |
| 350 | 4.1 | 6 | 60.7 |
| | | 20 | 28.7 |
| | | 40 | 21.6 |
| | | 60 | 21.0 |

This activity compares favourably with that of a Houdry silica-alumina catalyst in the form of 4–7 mm × 4 mm diameter extrusions (surface area 103 $m^2 g^{-1}$), tested for cumene cracking at 450° C and WHSV 4.0 gg$^{-1}$hr$^{-1}$:

TABLE 4

| Time (min) | Cumene Conversion (mole %) |
|---|---|
| 6 | 69.4 |
| 20 | 55.1 |
| 40 | 49.5 |
| 60 | 42.1 |

EXAMPLE 4

Zirconia/calcium oxide solid solution: 110.9 g zirconyl nitrate (40% $ZrO_2$), 11.8 g calcium nitrate ($Ca(NO_3)_2 4H_2O$) and 121.6 g citric acid were dissolved in about 400 ml water and dried under vacuum at 100° C. The solid product was calcined in air at 550° C for 6.5 hr. Excess CaO was removed by water extraction in a Soxhlet apparatus for 16 hr and the product was dried at 100° C. Its percentage composition by weight was $ZrO_2$, 91.8%; CaO, 4.4% C, 0.2% S, 0.9%; loss at 900° C 3.3%. Its surface area before water extraction was 46 $m^2/g$ and after water extraction, 89 $m^2/g$. An X-ray diffraction examination showed it to be cubic zirconia of lattice parameter about 5.12A, and crystallite size about 60A. The element analysis corresponds to zirconia/calcium solid solution containing 9.5 mole % CaO. The X-ray diffraction results indicate a cubic zirconia solid solution containing about 16 mole % CaO. The catalyst was pelleted in ⅛ inch pellets; later it was treated with boiling 1N nitric acid for 6 hr (for the purpose of removing traces of alkali metal), again extracted with water in a soxhlet apparatus for 16 hr and dried at 110° C. The catalyst was tested for acidic activity in cumene cracking, with percentage conversions as shown in Table 5. The surface area of the catalyst after two runs was 63 $m^2/g$. It is evident from a comparison of the 60 minute activity at 450° C with the 6 minute activity at 400° C that calcination after each run, as mentioned in the introduction to these Examples restores the activity of the catalyst.

TABLE 5

| Reactor Temperature ° C | WHSV g/g hr | Time min | Cumene Conversion mole % |
|---|---|---|---|
| 450 | 4.0 | 6 | 53.1 |
|  |  | 20 | 30.4 |
|  |  | 40 | 21.4 |
|  |  | 60 | 10.9 |
| 400 | 4.0 | 6 | 33.5 |
|  |  | 20 | 27.1 |
|  |  | 40 | 24.0 |
|  |  | 60 | 21.0 |

A further sample was prepared by the same technique including nitric acid treatment and tested for activity in both cumene cracking and o-xylene isomerisation.

TABLE 6

| Reactor Temperature ° C | WHSV g/g hr | Time min | Cumene Conversion mole % |
|---|---|---|---|
| 450 | 3.6 | 6 | 63.4 |
|  |  | 20 | 31.8 |
|  |  | 40 | 13.5 |
|  |  | 60 | 7.1 |

TABLE 7

| Reactor Temp. | WHSV g/g hr | Time hr | Conversion mole % | Pass yield, mole % | |
|---|---|---|---|---|---|
|  |  |  |  | p- + m-xylene | toluene |
| 450 | 0.22 | 0.5 | 27.3 | 20.1 | 7.2 |
|  |  | 1.0 | 38.1 | 25.8 | 12.3 |
|  |  |  |  | (4.4 p-xylene) |  |
|  |  |  |  | (21.4 m-xylene) |  |
|  |  | 1.5 | 17.7 | 9.5 | 8.2 |
|  |  | 2.0 | 9.8 | 4.0 | 5.8 |
|  |  | 2.5 | 5.9 | 1.8 | 4.1 |
|  |  | 3.0 | 3.9 | 1.0 | 2.9 |
|  |  | 4.0 | 2.1 | 0.4 | 1.7 |
|  |  | 6.0 | 1.3 | 0.3 | 1.0 |

EXAMPLE 5

Zirconia/samaria solid solution 0.349 samaria ($Sm_2O_3$) followed by 24.4 g zirconyl nitrate were dissolved in about 100 ml dilute nitric acid. 28.14 g citric acid were dissolved separately in about 25 ml water and added to the mixed nitrate solution. The preparation was continued as in Example 4, including treatment with nitric acid. The weight percentage composition of the product was $ZrO_2$ 89.5; $Sm_2O_3$ 2.9; S 0.5; loss at 900° C 6.0. The metal atom percentage of samarium was 2.2. The specific surface was 95 $m^2/g$. The catalyst was tested for activity in cumene cracking (Table 8) and o-xylene isomerisation (Table 9).

TABLE 8

| Reactor Temperature ° C | WHSV g/g hr | Time min | Cumene Conversion mole % |
|---|---|---|---|
| 450 | 3.2 | 7 | 71.0 |
|  |  | 20 | 29.8 |
|  |  | 40 | 21.2 |
|  |  | 60 | 3.3 |
| 400 | 3.5 | 6 | 58.2 |
|  |  | 20 | 33.1 |
|  |  | 40 | 22.4 |
|  |  | 60 | 17.9 |

TABLE 9

| Reactor Temperature ° C | WHSV g/g hr | Time hr | o-xylene isomerisation Conversion mole % | Pass yield, mole % | |
|---|---|---|---|---|---|
|  |  |  |  | p- + m-xylene | toluene |
| 450 | 0.22 | 0.5 | 17.2 | 14.5 | 2.7 |
|  |  | 1.0 | 25.5 | 18.1 | 7.4 |
|  |  |  |  | (2.1, p-xylene) |  |
|  |  |  |  | (16.0, m-xylene) |  |
|  |  | 1.5 | 15.0 | 8.8 | 6.2 |
|  |  | 2.0 | 9.2 | 4.6 | 4.6 |
|  |  | 2.5 | 6.1 | 2.6 | 3.5 |
|  |  | 3.0 | 4.7 | 1.5 | 3.2 |
|  |  | 4.0 | 2.4 | 0.6 | 1.8 |
|  |  | 6.0 | 1.1 | 0.3 | 0.8 |

EXAMPLE 6

Zirconia/yttria solid solution: 10.0 g yttrium nitrate (Y(No$_3$)$_3$6H$_2$O) and 28.9 g zirconyl nitrate (40% ZrO$_2$) were dissolved in about 100 ml water, mixed with 38.4 g citric acid dissolved in about 25 ml water, and treated as in Example 4. The surface area after water extraction was 96 m$^2$/g. The composition of the catalyst by weight was ZrO$_2$ 78.7%; Y$_2$O$_3$ 15.1%; S 0.3%; loss at 900° C 4.5%. The metal atom percentage of yttrium was 17.2%.

The catalyst was tested for activity in cumene cracking (a) before and (b) after nitric acid treatment.

TABLE 10

| | Reactor Temperature °C | Cumene cracking WHSV g/g hr | Time min | Cumene Conversion mole % |
|---|---|---|---|---|
| (a) | 500 | 3.2 | 20 | 0.62 |
| | | | 40 | 0.34 |
| | | | 60 | 0.29 |
| (b) | 450 | 3.5 | 6 | 60.6 |
| | | | 20 | 36.4 |
| | | | 60 | 9.6 |
| | 400 | 3.5 | 6 | 23.7 |
| | | | 20 | 19.7 |
| | | | 40 | 17.4 |
| | | | 60 | 16.0 |

EXAMPLE 7

Zirconia/dysprosia catalyst

A catalyst was prepared from 10.0 g dysprosia (Dy$_2$O$_3$), 14.5 g nitric acid, 59.5 g zirconyl nitrate and 78.9 citric acid by the method of Example 5. The surface area was 80 m$^2$/g. The percentage composition of the catalyst by weight was ZrO$_2$ 72; Dy$_2$O$_3$ 22.6; S 0.3; loss at 900° C 4.2. The metal atom percentage of dysprosium was 17.2%. The catalyst was tested for activity in cumene cracking, with the following results.

TABLE 11

| Reactor Temperature °C | WHSV g/g hr | Time min | Cumene Conversion mole % |
|---|---|---|---|
| 450 | 3.7 | 6 | 75.0 |
| | | 20 | 34.3 |
| | | 40 | 14.0 |
| | | 60 | 6.0 |
| 400 | 3.7 | 6 | 47.1 |
| | | 20 | 35.2 |
| | | 40 | 27.4 |
| | | 60 | 23.2 |
| 350 | 3.7 | 6 | 25.6 |
| | | 20 | 26.3 |
| | | 40 | 22.3 |
| | | 60 | 14.8 |

EXAMPLE 8

Zirconia/manganese Oxide Solid Solution

Zirconyl carbonate was dissolved in nitric acid, mixed with manganous nitrate solution and then added to a solution containing a molar excess of ammonia to co-precipitate the product. This product was filtered, washed, dried and then calcined at 650° C. The calcined material contained 4.1 wt % Mn, 0.010 wt % Na, 0.16 wt % S, and had a loss at 900° C of 4.0 wt %. The surface area was 55 m$^2$ g$^{-1}$, and an X-ray diffraction examination showed the presence of a cubic/tetragonal solid solution of lattice parameter 5.09 A and crystallite size about 110A. The activity for cumene cracking is shown in Table 12 hereafter. The following examples 9 to 14 are of zirconia-containing solid solutions with other acidic, anionic co-catalysts, and containing only negligible amounts of sulphate.

EXAMPLE 9

Zirconia/yttria solid solution with phosphate co-catalyst. Zirconyl carbonate was dissolved in nitric acid, mixed with yttrium nitrate solution and the product coprecipitated with ammonia solution. The product was filtered, washed, dried and then stood in a 1.0 M solution of triammonium phosphate for several hours. The product was then filtered, washed, dried and calcined at 750° C. The calcined material contained 75.4 wt % ZrO$_2$, 3.9 wt % Y$_2$O$_3$, 12.8 wt % P$_2$O$_5$, 0.0076 wt % Na and less than 0.02 wt % S. The surface area was 30 m$^2$ g$^{-1}$, and an X-ray diffraction examination showed the presence of a cubic solid solution of mean lattice parameter 5.115 A. The activity for cumene cracking is shown in Table 12 hereafter.

A series of catalysts was prepared in which zirconyl carbonate was dissolved in aqueous acetic acid (15% vt/vol), the solution brought to the boil, barium chloride solution (20% wt/vol) added to give an excess of barium relative to sulphate, the mixture allowed to stand at around 80° C for 1 hour and then the barium sulphate removed by filtration. Aluminium nitrate solution was added to the purified zirconium solution and the hydrous oxides coprecipitated with ammonia solution. The product was filtered, washed four times with hot water to remove any barium oxide and dried. The product was then impregnated with the anionic co-catalyst, either as the acid or as the ammonium salt, dried and calcined at 750° C.

EXAMPLE 10

Zirconia/alumina solid solution with phosphate co-catalyst

The dried product was impregnated with triammonium phosphate. The calcined product contained 7.5 wt % Al$_2$O$_3$, 15.4 wt % P$_2$O$_5$, 0.01 wt % S, and had a loss at 900° C of 1.3 wt %. The surface area was 30 m$^2$ g$^{-1}$, and X-ray diffraction showed a cubic solid solution of lattice parameter 5.08A. The activity for cumene cracking is shown in Table 12 hereafter.

EXAMPLE 11

Zirconia/alumina solid solution with fluoride co-catalyst

The dried product was impregnated with ammonium fluoride. The calcined product contained 7.5 wt % Al$_2$O$_3$, 0.3 wt % F and 0.01 wt % S. The surface area was 17 m$^2$ g$^{-1}$, and the structure was the same as in Example 10. The activity for cumene cracking is shown in Table 12 hereafter.

EXAMPLE 12

Zirconia/alumina solid solution with chloride co-catalyst

The dried product was impregnated with hydrochloric acid. The calcined product contained 7.5 wt % Al$_2$O$_3$, 4.8 wt % Cl and 0.01 wt % S. The surface area was 40 m$^2$ g$^{-1}$, and the structure was the same as in Example 10. The activity for cumene cracking is shown in Table 12 hereafter.

EXAMPLE 13

Zirconia/alumina solid solution with sulphate and phosphate co-catalysts. Zirconyl carbonate was dissolved in nitric acid, mixed with aluminum nitrate solution and the product washed, dried and then impregnated with triammonium phosphate, followed by drying and calcining at 750° C. The calcined product contained $Al_2O_3$ 8.2 wt %, S 0.25 wt %, $P_2O_5$ 8.0 wt %, $Na_2O$ less than 0.01 wt %, and had a loss at 900° C of 1.1 wt %. The surface area was 109 $m^2 g^{-1}$, and X-ray diffraction showed a cubic solid solution of mean lattice parameter 5.086A. The activity for cumene cracking is shown in Table 12 hereafter.

EXAMPLE 14

Zirconia/alumina solid solution with silica co-catalyst

Zirconyl carbonate was dissolved in nitric acid, mixed with aluminium nitrate solution and the product coprecipitated with ammonia solution. The product was filtered, washed, dried and calcined at 750° C before impregnating with silica by refluxing it with tetra ethyl silicate in isoctane and distilling off the ethanol produced. The product was then dried and calcined at 500° C. The product then contained $Al_2O_3$ 11.1 wt %, $SiO_2$ 4.5 wt % and S 0.07 wt %. The surface area was 49 $m^2 g^{-1}$ and X-ray diffraction showed a cubic solid solution of lattice parameter 5.09A. The activity for cumene cracking is shown in Table 12 hereafter.

Other solid solution systems, apart from those based on zirconia, also showed acidic activity, both with and without the presence of co-catalysts. Two such systems are shown in the following examples 15 to 17.

EXAMPLE 15

Tin oxide/antimony oxide solid solution

Tin tetrachloride and antimony pentachloride were mixed and added dropwise to a molar excess ammonia solution at 0° C under flowing nitrogen. The final pH was greater than 8.5. The product was washed, dried, and calcined at 650° C. The calcined product contained 3 wt % $Sb_2O_5$, and X-ray diffraction showed the cassiterite structure with a slight shift in line pattern and no evidence of any antimony compounds. The activity for cumene cracking is shown in Table 12 hereafter.

EXAMPLE 16

Chromia/tungsten oxide solid solution

Chromium nitrate solution was added to a solution of ammonium tungstate mixed with sufficient ammonia solution to give a final pH of 7 at the end of the precipitation. The product was filtered, washed, dried and calcined at 650° C. The calcined product contained 26.0 wt % $WO_3$, less than 0.005 wt % Na, and had a loss at 600° C of 0.6 wt %. The X-ray diffraction pattern was compared with the ASTM data for chromia and the main differences were:

a. The lines in the chromia-tungsten oxide catalyst were distinctly shifted to lower d spacings indicating a decrease in lattice parameter.

b. Significant variations in the relative intensities of the lines were observed.

These results indicated the presence of a chromia-tungsten oxide solid solution. The activity for cumene cracking is shown in Table 12 hereafter.

EXAMPLE 17

Chromia/tungsten oxide solid solution with phosphate co-catalyst

Chromia and tungsten oxide were coprecipitated as in the previous example and the dried product was impregnated with triammonium phosphate, dried and calcined at 650° C. The calcined product contained 2.1 wt % $P_2O_5$. The activity for cumene cracking is shown in Table 12 hereafter.

If desired, any of these crystalline solid solutions, with or without co-catalysts, can be incorporated with a matrix or supported on a carrier to give a final catalyst which may, for example, have a higher surface area, greater heat or steam stability, lower manufacturing cost, lower density, and other advantages.

EXAMPLE 18

Zirconia/Magnesia solid solution supported on alumina

Some spray-dried alumina powder was calcined at 500° C, acid-washed to remove traces of sodium, impregnated with magnesium nitrate solution, dried, calcined at 600° C, impregnated with a solution obtained by dissolving zirconium carbonate in sulphuric acid, dried and calcined at 750° C. The final catalyst contained 56.0 wt % $Al_2O_3$, 14.6 wt % $ZrO_2$, 7.0 wt % MgO, 5.5 wt % S, and 0.10% $Na_2O$. The surface area was 50 $m^2 g^{-1}$, and an X-ray diffraction examination showed the following phases:

a. $\gamma$-$Al_2O_3$, no $Al_2O_3$/MgO solid solution b. Cubic zirconia solid solution with a lattice parameter of 5.085A.

This indicated that the catalyst consisted of a cubic zirconia-magnesia solid solution supported on alumina. The activity for cumene cracking is shown in Table 12 hereafter.

TABLE 12

Cumene Cracking at 450° C
Atmospheric Pressure and WHSV 4.3 $gg^{-1} h^{-1}$

| Example | Cumene Conversion (mole %) | | | |
|---|---|---|---|---|
| | Time (mins) 6 | 20 | 40 | 60 |
| 8 | 15.0 | 10.6 | 7.6 | 5.8 |
| 9 | 44.7 | 20.3 | 16.2 | 13.4 |
| 10 | 41.9 | 25.0 | 19.0 | 17.6 |
| 11 | 59.6 | 48.5 | 48.0 | 47.4 |
| 12 | 20.3 | 15.5 | 13.4 | 12.0 |
| 13 | 59.1 | 41.9 | 37.9 | 36.7 |
| 14 | 38.5 | 31.9 | 30.1 | 27.2 |
| 15 | 5.3 | 4.2 | 3.7 | 3.1 |
| 16 | 17.5 | 3.0 | 1.4 | 1.1 |
| 17 | 40.5 | 3.9 | 2.0 | 1.6 |
| 18 | 59.2 | 41.9 | 33.1 | 31.9 |

We claim:

1. An acidic catalyst for treating hydrocarbons consisting essentially of a crystalline solid solution in zirconia of an irreducible oxide of a lower valency metal selected from the group consisting of magnesium, aluminum, yttrium, calcium, manganese and rare earth metal, wherein the zirconia is present in solution in excess by atoms so that the crystal lattice of the zirconia is made defective by the presence of the oxide of the selected lower valency metal, the percentage by metal atoms of the selected lower valency metal in the solution being in the range 0.05% to 30%; and wherein the crystalline solid solution also contains an acidic co-catalyst in a proportion of 0.1 to 20% by weight, said co-catalyst being silica, boria or an ion selected from the group consisting of sulphate, chloride, fluoride, and phosphate, said ion being chemically combined with the solid solution.

2. A catalyst as claimed in claim 1, wherein said oxide of a rare earth metal is samaria or dysprosia.

3. A catalyst according to claim 1 wherein the percentage of lower valency metal by atoms in solution is between 1 and 30%.

4. A catalyst according to claim 3 wherein the percentage of lower valency metal by atoms in solution is between 5 and 25%.

5. A catalyst according to claim 1 wherein the lattice has a concentration of defects greater than 1% of the total lattice pites.

6. A catalyst according to claim 1, wherein the proportion of acidic co-catalyst is from 0.5 to 20% by weight.

* * * * *